US011029754B2

(12) United States Patent
Yamada

(10) Patent No.: US 11,029,754 B2
(45) Date of Patent: Jun. 8, 2021

(54) CALIBRATION METHOD, PORTABLE DEVICE, AND COMPUTER-READABLE STORAGE MEDIUM

(71) Applicant: ALPS ALPINE CO., LTD., Tokyo (JP)

(72) Inventor: Yukimitsu Yamada, Miyagi (JP)

(73) Assignee: ALPS ALPINE CO., LTD., Tokyo (JP)

( * ) Notice: Subject to any disclaimer, the term of this patent is extended or adjusted under 35 U.S.C. 154(b) by 706 days.

(21) Appl. No.: 15/936,865

(22) Filed: Mar. 27, 2018

(65) Prior Publication Data

US 2018/0217664 A1 Aug. 2, 2018

Related U.S. Application Data

(63) Continuation of application No. PCT/JP2016/083798, filed on Nov. 15, 2016.

(30) Foreign Application Priority Data

Nov. 30, 2015 (JP) .............................. JP2015-233028

(51) Int. Cl.
*G06F 3/01* (2006.01)
*A61B 5/11* (2006.01)
(Continued)

(52) U.S. Cl.
CPC ................ *G06F 3/012* (2013.01); *A61B 5/11* (2013.01); *A61B 5/1114* (2013.01); *A61B 5/24* (2021.01);
(Continued)

(58) Field of Classification Search
CPC .. G06F 3/012; A61B 5/24; A61B 5/11; H04N 13/344; H04N 5/232939; G02B 27/0093
See application file for complete search history.

(56) References Cited

U.S. PATENT DOCUMENTS 8,217,856 B1 * 7/2012 Petrou ..................... G06F 3/011
345/8
2007/0015611 A1 1/2007 Noble et al.
(Continued)

FOREIGN PATENT DOCUMENTS

| JP | 2013-165403 | 8/2013 |
| WO | 2012/026375 | 3/2012 |
| WO | 2015/159853 | 10/2015 |

OTHER PUBLICATIONS

International Search Report dated Jan. 24, 2017 in PCT/JP2016/083798 filed on Nov. 15, 2016.
(Continued)

*Primary Examiner* — Said Broome
(74) *Attorney, Agent, or Firm* — IPUSA, PLLC

(57) ABSTRACT

A tilt adjusting image including a captured image that is obtained by capturing a wearer wearing a spectacle-type electronic device, and a horizontal line image indicating a horizontal direction identified by a tilt identification part, is displayed. The wearer adjusts a position of the spectacle-type electronic device by a wearer's hand or the like while viewing the tilt adjusting image so that the spectacle-type electronic device becomes horizontal. When the wearer judges that the spectacle-type electronic device has become horizontal, the wearer operates an operation part and inputs a calibration instruction. When the calibration instruction is input, the calibration instruction is transmitted to the spectacle-type electronic device.

14 Claims, 8 Drawing Sheets

(51) Int. Cl.

| | |
|---|---|
| *H04N 5/232* | (2006.01) |
| *A61B 5/00* | (2006.01) |
| *G02B 27/00* | (2006.01) |
| *H04N 13/344* | (2018.01) |
| *A61B 5/24* | (2021.01) |
| *G12B 13/00* | (2006.01) |
| *G02B 27/01* | (2006.01) |

(52) U.S. Cl.
CPC ........ *A61B 5/6803* (2013.01); *G02B 27/0093* (2013.01); *G12B 13/00* (2013.01); *H04N 5/23293* (2013.01); *H04N 5/232939* (2018.08); *H04N 13/344* (2018.05); *A61B 2560/0223* (2013.01); *G02B 2027/0138* (2013.01)

(56) References Cited

U.S. PATENT DOCUMENTS

| | | |
|---|---|---|
| 2012/0182521 A1 | 7/2012 | Kubitza et al. |
| 2014/0232981 A1 | 8/2014 | Sugihara |
| 2015/0015461 A1* | 1/2015 | Morimoto ............ G02B 27/017 345/8 |

OTHER PUBLICATIONS

Extended European Search Report for 16870431.0 dated Nov. 19, 2018.

\* cited by examiner

500

CALIBRATION METHOD, PORTABLE DEVICE, AND COMPUTER-READABLE STORAGE MEDIUM

CROSS-REFERENCE TO RELATED APPLICATIONS

This application is a continuation application filed under 35 U.S.C. 111(a) claiming the benefit under 35 U.S.C. 120 and 365(c) of a PCT International Application No. PCT/JP2016/083798 filed on Nov. 15, 2016, which is based upon and claims the benefit of priority of the prior Japanese Patent Application No. 2015-233028 filed on Nov. 30, 2015, the entire contents of which are incorporated herein by reference.

BACKGROUND OF THE INVENTION

1. Field of the Invention

The present invention relates to a calibration method that calibrates an acceleration sensor of a spectacle-type electronic device, a portable device, and a computer-readable storage medium.

2. Description of the Related Art

There is a spectacle-type electronic device provided with a sensor, such as an acceleration sensor or the like. In such a spectacle-type electronic device, a position or the like of a head when walking is detected based on acceleration detected by the acceleration sensor, and utilized for analysis.

The position when walking can be identified by detecting an error with respect to a body axis when walking, for example, with reference to an absolute axis (gravity) direction.

Errors, caused by an offset error at a time of assembly and sensitivity, are generated in the acceleration sensor. Hence, calibration is required to correct such errors.

The calibration is performed under a precondition that, a wearer is stationary and takes a position in which the wearer's face faces frontward, and the spectacle-type electronic device is horizontal in this position, for example.

However, even in a case where the wearer takes the position in which the wearer's face faces frontward when performing the calibration, the spectacle-type electronic device may not be horizontal due to causes such as slipping from a wearing position of the spectacle-type electronic device, a skew of the wearer himself from the absolute axis (gravity), unanticipated tilt of the head, or the like. In this case, there is a problem in that the calibration cannot be performed appropriately.

SUMMARY OF THE INVENTION

Accordingly, it is an object in one aspect of the embodiments to provide a calibration method, a portable device, and a computer-readable storage medium that can perform a highly accurate calibration of the acceleration sensor provided in the spectacle-type electronic device.

According to one aspect of embodiments of the present invention, a calibration method includes a first step identifying a predetermined tilt with respect to a gravity direction based on an acceleration detected by a first acceleration sensor provided in a portable device, a second step displaying, on a display of the portable device, a tilt adjusting image for adjusting a tilt of a spectacle-type electronic device, based on an image of a wearer of the spectacle-type electronic device captured by the portable device and the predetermined tilt that is identified, and a third step performing a calibration of a second acceleration sensor provided in the spectacle-type electronic device under a condition that a tilt of the spectacle-type electronic device is adjusted.

According to another aspect of the embodiments of the present invention, a portable device includes a capturing device configured to capture an image of a wearer wearing a spectacle-type electronic device, q first acceleration sensor, and a processor configured to perform a process including identifying a predetermined tilt with respect to a gravity direction based on an acceleration detected by the first acceleration sensor, displaying, on a display, a tilt adjusting image for adjusting a tilt of the spectacle-type electronic device, based on the image that is captured and the predetermined tilt that is identified, and transmitting, to the spectacle-type electronic device, a calibration instruction that instructs calibration of a second acceleration sensor of the spectacle-type electronic device, under a condition that a tilt of the spectacle-type electronic device is adjusted.

According to still another aspect of the embodiments of the present invention, a non-transitory computer readable storage medium has stored therein a program which, when executed by a computer of a portable device, causes the computer to perform a calibration process including a first procedure identifying a predetermined tilt with respect to a gravity direction based on an acceleration detected by a first acceleration sensor provided in a portable device, a second procedure displaying, on a display of the portable device, a tilt adjusting image for adjusting a tilt of a spectacle-type electronic device, based on an image of a wearer of the spectacle-type electronic device captured by the portable device and the predetermined tilt that is identified, and a third procedure performing a calibration of a second acceleration sensor provided in the spectacle-type electronic device under a condition that a tilt of the spectacle-type electronic device is adjusted.

Other objects and further features of the present invention may be apparent from the following detailed description when read in conjunction with the accompanying drawings.

DESCRIPTION OF THE PREFERRED EMBODIMENTS

First Embodiment

A calibration method in a first embodiment of the present invention will be described.

According to the calibration method in the first embodiment, a wearer of a spectacle-type electronic device 1 takes an image of himself by a camera of a portable electronic device 81, and adjusts a position of the spectacle-type electronic device 1 to become horizontal while viewing the image of himself. In a case in which the spectacle-type electronic device 1 becomes horizontal, a calibration instruction is issued with respect to the spectacle-type electronic device 1, to perform calibration of an acceleration sensor 71 of the spectacle-type electronic device 1.

Next, the spectacle-type electronic device 1 in the first embodiment of the present invention will be described.

Figure 1:
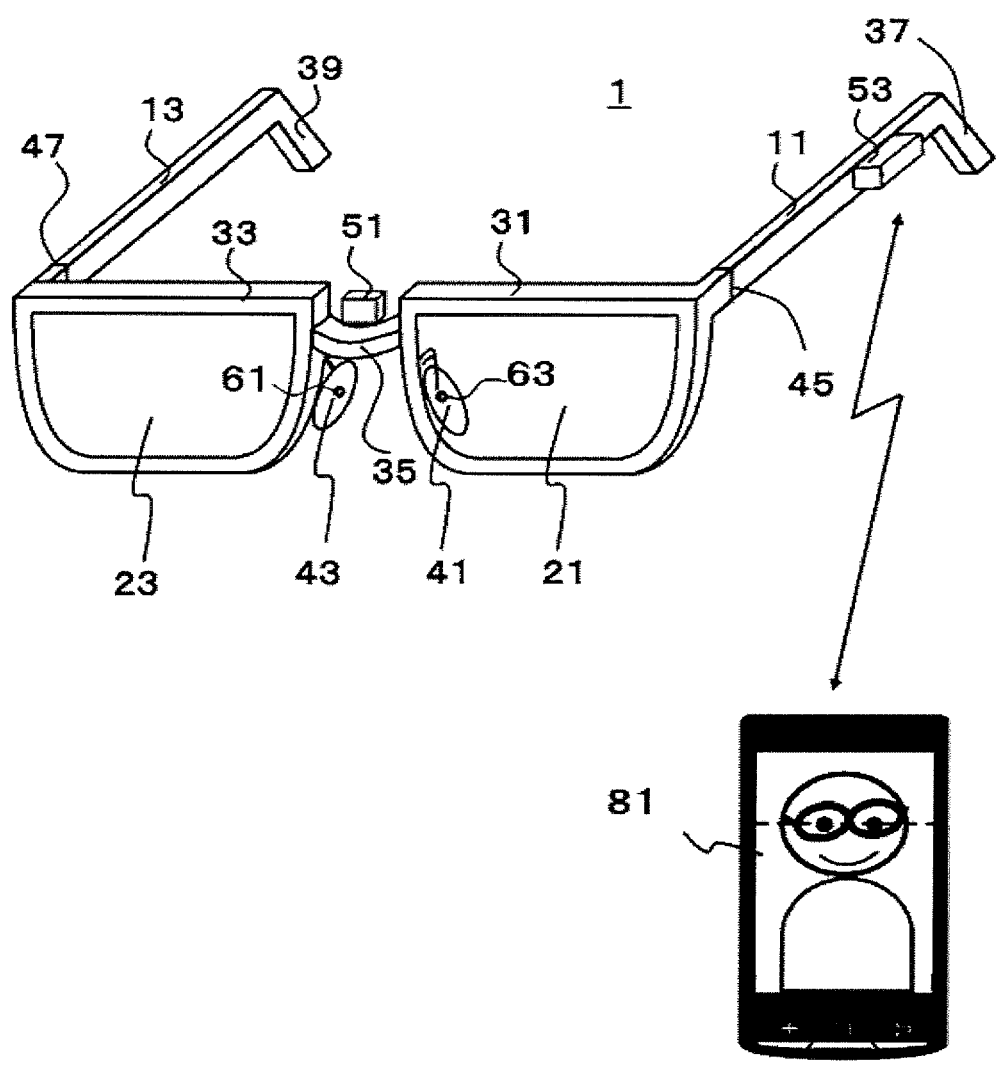
FIG. 1 is a external perspective view of a spectacle-type electronic device in a first embodiment of the present invention.
Figure 2:
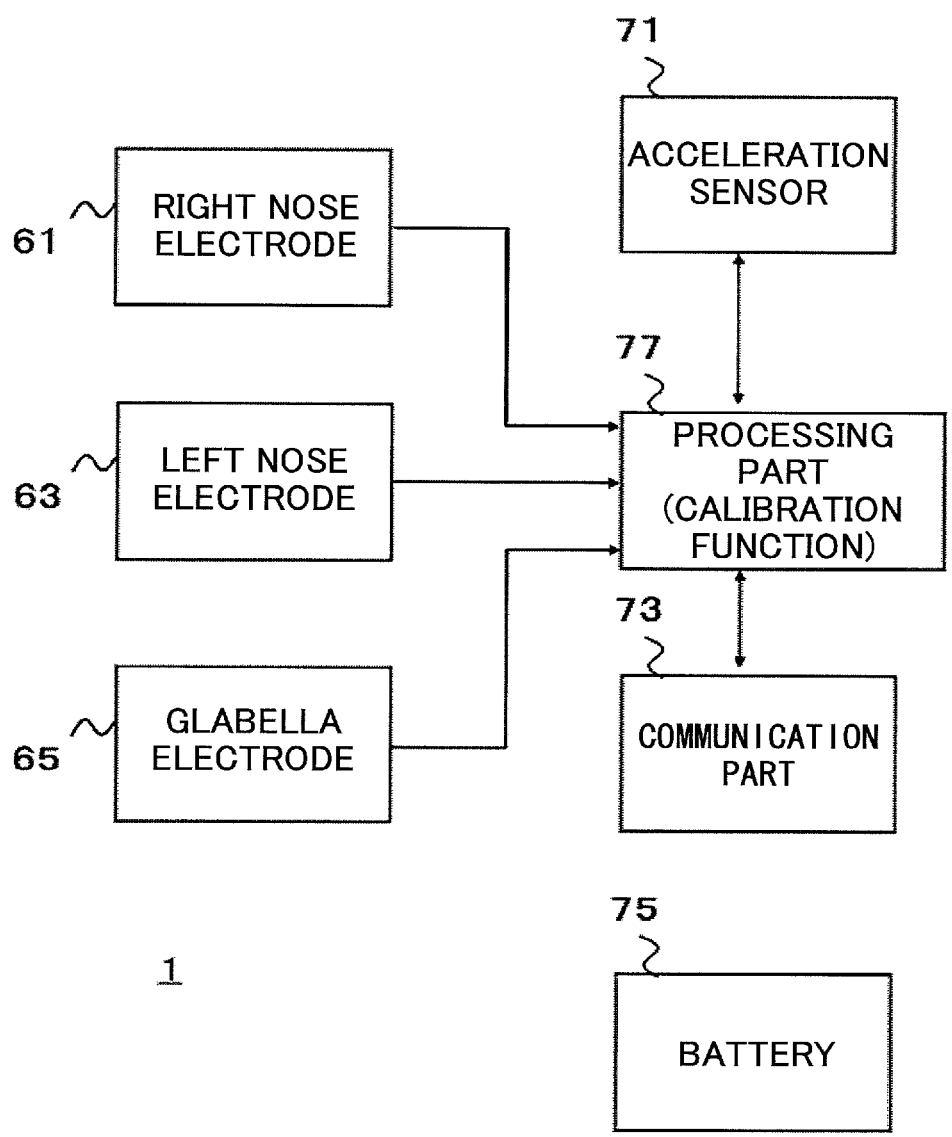
FIG. 2 is a functional block diagram of the spectacle-type electronic device illustrated in FIG. 1.

FIG. 1 is a external perspective view of the spectacle-type electronic device 1 in the first embodiment of the present invention. FIG. 2 is a functional block diagram of the spectacle-type electronic device 1 illustrated in FIG. 1.

As illustrated in FIG. 1, the spectacle-type electronic device 1 has temples 11 and 13, rims 31 and 33 to which lenses 21 and 23 are fixed, a bridge 35 interposed between the rims 31 and 33, and nose pads 41 and 43. Tip ends of the rims 31 and 33 are called temple tips 37 and 39. In addition, a hinge 45 is provided between the temple 11 and the rim 31, and a hinge 47 is provided between the temple 13 and the rim 33.

As illustrated in FIG. 2, an accommodation box 51 is provided between the nose pads 41 and 43.

Further, an accommodation box 53 is fixed to the temple 11 near the temple tip 37.

A right nose electrode 61 is provided on a surface of the nose pad 41, and a left nose electrode 63 is provided on a surface of the nose pad 43.

The right nose electrode 61 makes contact with (is pushed against) a right side surface of a ridge of a user's nose in a state in which the user wears the spectacle-type electronic device 1, and detects an electric potential of an eye, that is an electric potential of the contacted skin.

The left nose electrode 63 makes contact with a left side surface of a ridge of the user's nose in the state in which the user wears the spectacle-type electronic device 1, and detects an electric potential of an eye, that is an electric potential of the contacted skin.

The right nose electrode 61 and the left nose electrode 63 are arranged at symmetrical positions when the user's nose is viewed from a front of the user using the spectacle-type electronic device 1.

A glabella electrode 65 is provided in the accommodation box 51. The glabella electrode 65 makes contact with a root of the user's nose or glabella in the state in which the user wears the spectacle-type electronic device 1, and detects an electric potential of the contacted skin.

The right nose electrode 61, the left nose electrode 63, and the glabella electrode 65 are formed by stainless steel or titanium, for example.

The right nose electrode 61, the left nose electrode 63, and the glabella electrode 65 are formed to have shapes suited for shapes of body parts to be contacted.

The accommodation box 53 has an internal accommodation space, and an acceleration sensor 71, a communication part 73, a battery 75, and a processing part 77 are accommodated within the accommodation space.

The accommodation box 51 and the accommodation box 53 are electrically connected by wirings of a printed circuit board or the like.

The acceleration sensor 71 is a 3-axis acceleration sensor that detects acceleration in X, Y, and Z axes, and the acceleration detected in each axis is output to the processing part 77. The acceleration sensor 71 detects the acceleration at predetermined detection time intervals. In this embodiment, the acceleration sensor 71 is located at a position in a periphery of an ear of a head, suited for detecting head movement, when the user wears the spectacle-type electronic device 1.

The communication part 73 can transmit the electric potentials of the eyes input from the right nose electrode 61, the left nose electrode 63, and the glabella electrode 65, the acceleration input from the acceleration sensor 71, or the like to an external device, by wireless communication such as Bluetooth (registered trademark) or the like.

In addition, the communication part 73 receives a calibration instruction signal from the portable electronic device 81, as will be described later.

The processing part 77 generates information related to the user, based on the electric potentials of the eyes input from the right nose electrode 61, the left nose electrode 63, and the glabella electrode 65, and the acceleration input from the acceleration sensor 71.

The electric potentials of the eyes (electric potentials of the skin) input from the right nose electrode 61, the left nose electrode 63, and the glabella electrode 65, and the acceleration input from the acceleration sensor 71 are electric potentials according to the user's sweating and movement, and reflect the user's physical condition, mental condition, or the like. For this reason, by preparing reference data in advance, indicating correspondence of the electric potentials of the eyes and the acceleration with respect to the user's physical condition and mental condition, the processing part 77 can compare the electric potentials of the user's eyes and acceleration that are input with the prepared reference data, and detect the user's physical condition and mental condition. Accordingly, the spectacle-type electronic device 1 exhibits a position analyzing function.

In an eyeball, a cornea side is positively charged, and a retina side is negatively charged. Accordingly, in a case in which a line of sight moves up, the electric potential of the eye at the right nose electrode 61 with reference to the electric potential of the eye at the glabella electrode 65, and the electric potential of the eye at the left nose electrode 63 with reference to the electric potential of the eye at the glabella electrode 65 become negative. On the other hand, in a case in which the line of sight moves down, the electric potential of the eye at the right nose electrode 61 with reference to the electric potential of the eye at the glabella electrode 65, and the electric potential of the eye at the left nose electrode 63 with reference to the electric potential of the eye at the glabella electrode 65 become positive.

In a case in which the line of sight moves to the right, the electric potential of the eye at the right nose electrode 61 with reference to the electric potential of the eye at the glabella electrode 65 becomes negative, and the electric potential of the eye at the left nose electrode 63 with reference to the electric potential of the eye at the glabella electrode 65 becomes positive.

In a case in which the line of sight moves to the left, the electric potential of the eye at the right nose electrode 61 with reference to the electric potential of the eye at the glabella electrode 65 becomes positive, and the electric potential of the eye at the left nose electrode 63 with reference to the electric potential of the eye at the glabella electrode 65 becomes negative.

Hence, it is possible to detect that the line of sight moved up in the case in which a positive electric potential of the eye is detected. In addition, it is possible to detect that the line of sight moved down in the case in which a negative electric potential of the eye is detected. In addition, it is possible to detect that the line of sight moved to the right in the case in which the electric potential of the eye from the right nose electrode 61 is negative, and the electric potential of the eye from the left nose electrode 63 is positive. Further, it is possible to detect that the line of sight moved to the left in the case in which the electric potential of the eye from the right nose electrode 61 is positive, and the electric potential of the eye from the left nose electrode 63 is negative.

The processing part 77 performs a calibration process to calibrate the acceleration sensor 71. More particularly, when the communication part 73 receives the calibration instruction signal from the portable electronic device 81, the processing part 77 judges that the position of the spectacle-type electronic device 1 at a timing when the calibration instruction signal is received is a horizontal state, and calibrates the acceleration sensor 71.

Next, the portable electronic device 81 that is used to calibrate the acceleration sensor 71 of the spectacle-type electronic device 1 will be described.

Figure 3:
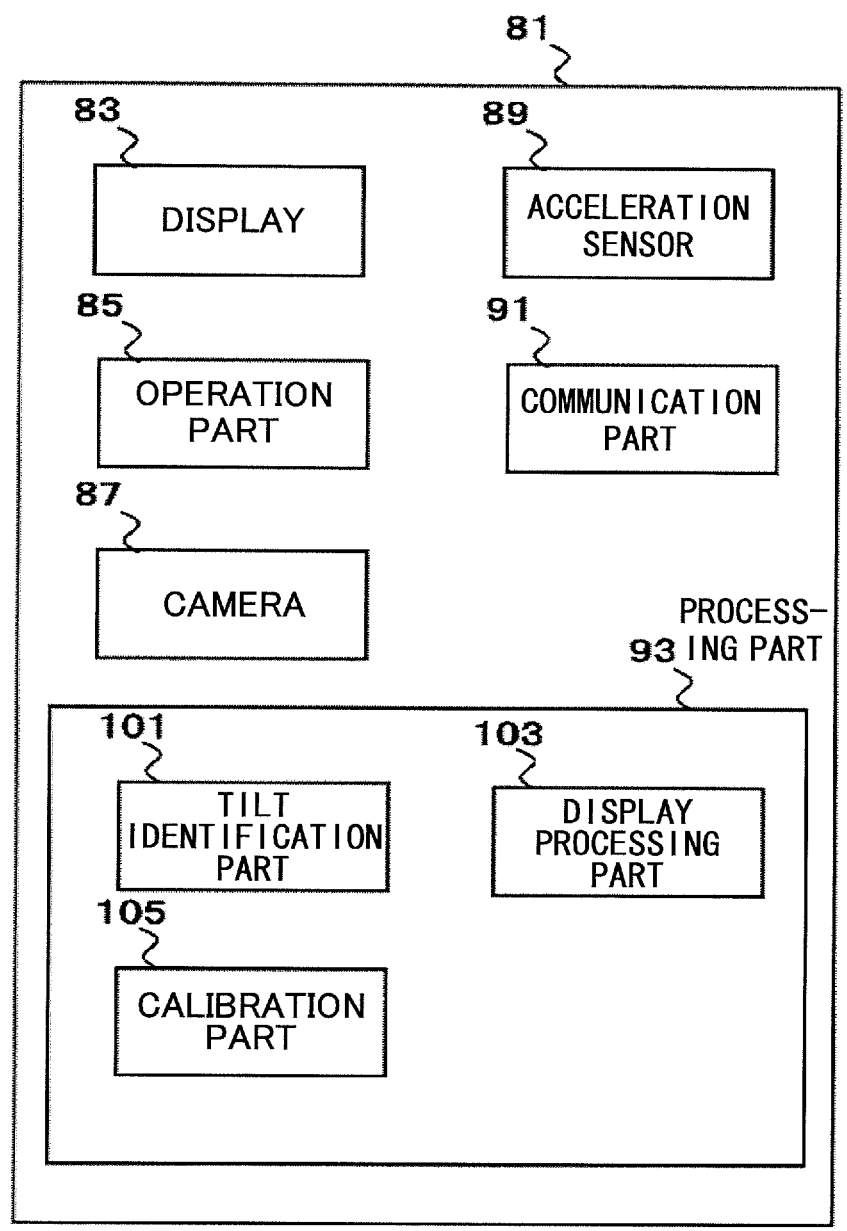
FIG. 3 is a functional block diagram of a portable electronic device in the first embodiment of the present invention.

FIG. 3 is a functional block diagram of the portable electronic device 81 in the first embodiment of the present invention.

As illustrated in FIG. 3, the portable electronic device 81 has a display 83, a operation part 85, a camera 87, an acceleration sensor 89, a communication part 91, and a processing part 93.

The camera 87 is an example of a capturing device that captures an image and outputs image data of the captured image to the processing part 93. In this embodiment, the image of the wearer (user) who wears the spectacle-type electronic device 1 is captured.

The acceleration sensor 89 is a 3-axis acceleration sensor that detects acceleration in X, Y, and Z axes, and the acceleration detected in each axis is output to the processing part 93.

The communication part 91 has functions for making near field communication such as Bluetooth (registered trademark), wireless LAN (Local Area Network) communication, or the like.

The processing part 93 has a tilt identification part 101, a display processing part 103, and a calibration part 105, for example.

A part of functions of the tilt identification part 101, the display processing part 103, and the calibration part 105 may be realized by hardware, or may be realized by executing a program by a processing circuit.

For example, the portable electronic device 81 uses the wireless LAN communication function of communication part 91, to download from a network an application program for performing the calibration, and stores the downloaded application program in a memory (not illustrated). The application program describes the functions of the tilt identification part 101, the display processing part 103, and the calibration part 105, and causes the processing part 93 to execute these functions.

The tilt identification part 101 identifies a predetermined tilt with respect to the gravity direction, based on the acceleration input from the acceleration sensor 89. In this embodiment, the tilt identification part 101 detects the horizontal direction.

Figure 4:
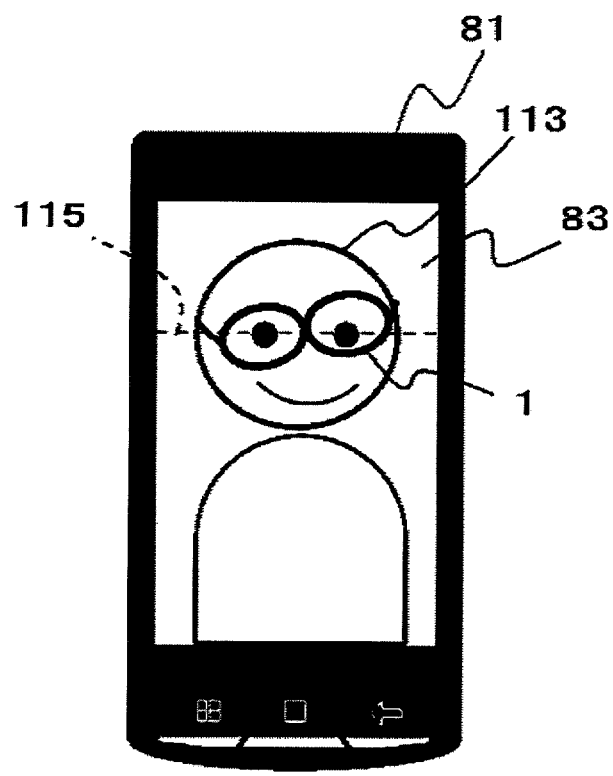
FIG. 4 is a diagram for explaining a tilt adjustment screen displayed on the portable electronic device before adjusting tilt of the spectacle-type electronic device illustrated in FIG. 1.
Figure 5:
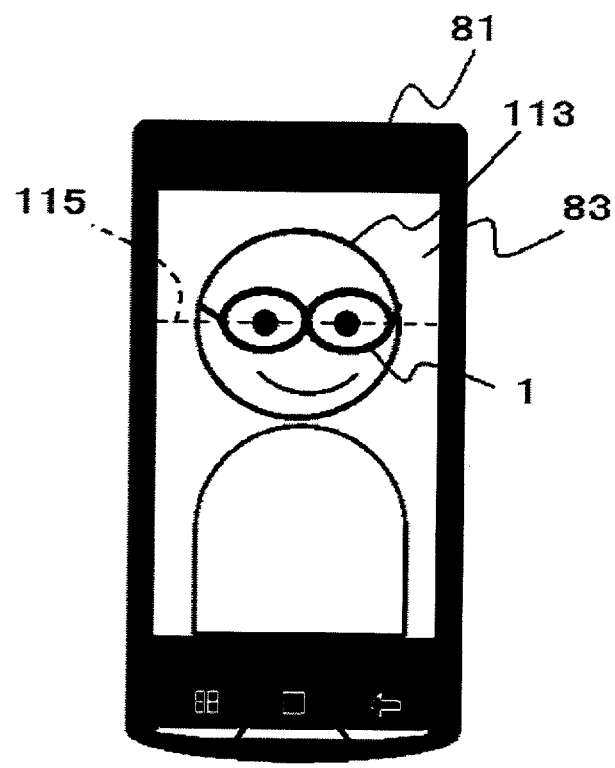
FIG. 5 is a diagram for explaining a tilt adjustment screen displayed on the portable electronic device after adjusting the tilt of the spectacle-type electronic device illustrated in FIG. 1.

The display processing part 103 generates image data of a tilt adjusting image, including a captured image 113 that is obtained by capturing the wearer (user) who wears the spectacle-type electronic device 1, and a horizontal line image 115 indicating the horizontal direction identified by the tilt identification part 101, as illustrated in FIG. 4, and outputs the image data of the tilt adjusting image to the display 83. Hence, the display 83 displays the tilt adjusting image that simultaneously includes the captured image 113 and the horizontal line image 115.

The calibration part 105 generates the calibration instruction signal under a condition that the tilt of the spectacle-type electronic device 1 becomes parallel to the horizontal direction (parallel to horizontal line image 115) in a state in which the tilt adjusting image is displayed on the display 83, and transmits the calibration instruction signal to the spectacle-type electronic device 1 via the communication part 91.

The spectacle-type electronic device 1 calibrates the acceleration sensor 71 as described above, based on the calibration instruction signal.

In other words, the calibration of the spectacle-type electronic device 1 is performed using the portable electronic device 81 as a master.

Next, an operation example of the calibration using the spectacle-type electronic device 1 and the portable electronic device 81 will be described.

Figure 6:
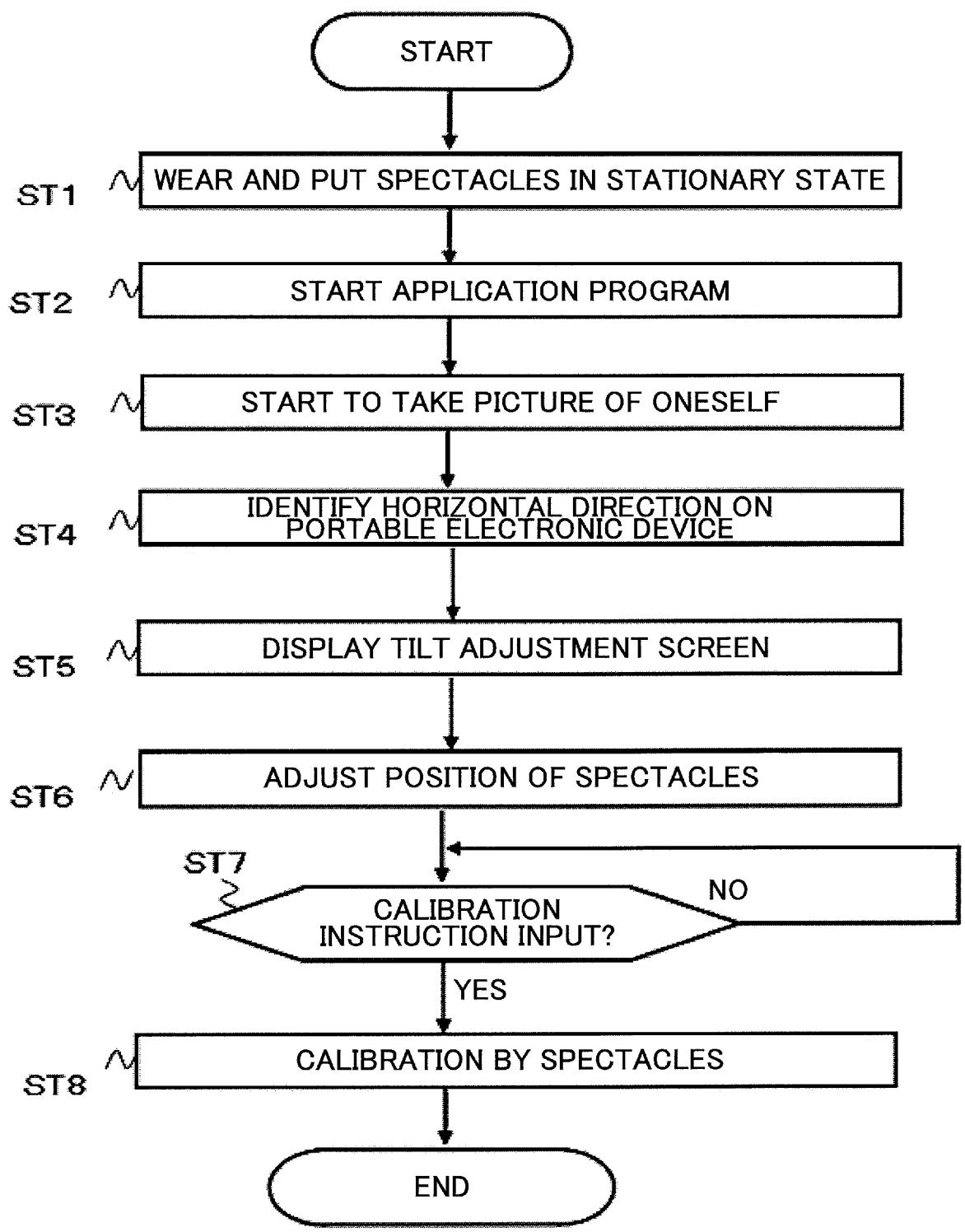
FIG. 6 is a flow chart for explaining an operation example of calibration in the first embodiment of the present invention.

FIG. 6 is a flow chart for explaining the operation example of calibration in the first embodiment of the present invention.

Step ST1:

The wearer of the spectacle-type electronic device 1 wears the spectacle-type electronic device 1, faces frontward, and puts the spectacle-type electronic device 1 in a stationary state.

Step ST2:

The wearer operates the operation part 85, and starts the application program for performing the calibration.

Step ST3:

The wearer starts to capture the wearer's face, including the spectacle-type electronic device 1, from the front using the camera 87.

Step ST4:

The tilt identification part 101 of the portable electronic device 81 identifies the predetermined tilt with respect to the gravity direction, based on the acceleration input from the acceleration sensor 89. In this embodiment, the tilt identification part 101 detects the horizontal direction. In this case, the spectacle-type electronic device 1 simply needs to be adjusted to the horizontal direction that is easy to ascertain visually, and the adjustment is facilitated.

Step ST5:

The display processing part 103 of the portable electronic device 81 generates the image data of the tilt adjusting image, including the captured image 113 that is obtained by capturing the wearer (user) who wears the spectacle-type electronic device 1, and the horizontal line image 115 indicating the horizontal direction identified by the tilt identification part 101, as illustrated in FIG. 4, and outputs the image data of the tilt adjusting image to the display 83. Hence, the tilt adjusting image illustrated in FIG. 4 is displayed on the display 83.

Step ST6:

The wearer adjusts the position of the spectacle-type electronic device 1 by a wearer's hand or the like, while viewing the tilt adjusting image displayed on the display 83, so that the spectacle-type electronic device 1 becomes horizontal with respect to the horizontal line image 115. When the wearer judges that the spectacle-type electronic device 1 has become horizontal with respect to the horizontal line image 115, the wearer operates the operation part 85 and inputs a calibration instruction. When the calibration instruction is input, the processing part 93 transmits the calibration instruction signal to the spectacle-type electronic device 1 via the communication part 91.

Step ST7:

When the processing part 77 of the spectacle-type electronic device 1 judges that the communication part 73 received the calibration instruction signal from the portable electronic device 81, the process advances to step ST8.

Step ST8:

When the communication part 73 receives the calibration instruction signal from the portable electronic device 81, the processing part 77 of the spectacle-type electronic device 1 judges that the position of the spectacle-type electronic device 1 at the timing when the calibration instruction signal is received is the horizontal state, and calibrates the acceleration sensor 71. Hence, the calibration of the acceleration sensor 71 is performed, to correct errors caused by an offset error at a time of assembly and sensitivity.

Accordingly, the wearer of the spectacle-type electronic device 1 can view the tilt adjusting image and start the calibration of the spectacle-type electronic device 1 at the timing when the spectacle-type electronic device assumes the adjusted state.

As described above, according to the calibration method in this embodiment, the tilt adjusting image illustrated in FIG. 4 is displayed on the display 83 of the portable electronic device 81 for the calibration. Hence, the wearer of the spectacle-type electronic device 1 can accurately adjust the position of the spectacle-type electronic device 1 by the wearer's hand while viewing the tilt adjusting image, so that the image of the spectacle-type electronic device 1 becomes parallel to the horizontal line image 113. For this reason, it is possible to accurately adjust the spectacle-type electronic device 1 to the horizontal state, and perform the calibration process in this horizontal state, to enable calibration of the acceleration sensor 71 with a high accuracy. In addition, the calibration of the acceleration sensor 71 of the spectacle-type electronic device 1 can be started when the tilt of the spectacle-type electronic device 1 is adjusted. Hence, the acceleration sensor 71 can be calibrated easily with a high accuracy.

In other words, even in a case in which a skew of the wearer himself from the absolute axis (gravity) exists, an accurate calibration can be performed because the spectacle-type electronic device 1 can be positioned in the horizontal state when performing the calibration.

In addition, the spectacle-type electronic device 1 has a superior design and may be worn on a daily basis without causing discomfort, because the acceleration sensor 71, the communication part 73, the battery 75, and the processing part 77 are accommodated with in the accommodation box 53.

Second Embodiment

In the first embodiment described above, the wearer judges whether the spectacle-type electronic device 1 has become parallel with respect to the horizontal line image 115. In a second embodiment, this judgment is automatically made by the portable electronic device 81.

In this embodiment, the calibration part 105 identifies the position of the spectacle-type electronic device 1 by performing an image analysis, based on the captured image 113 illustrated in FIG. 4 that is obtained by capturing the wearer by the camera 87. More particularly, the calibration part 105 detects, within the captured image 113, a plurality of feature points of an image of the spectacle-type electronic device 1 that is stored in advance, and identifies the position of the spectacle-type electronic device 1 based on a positional relationship of the detected feature points.

The calibration part 105 compares the horizontal direction identified by the tilt identification part 101 and the position of the spectacle-type electronic device 1 identified based on the feature points described above, and continuously performs the process of judging whether the spectacle-type electronic device 1 has become horizontal.

The calibration part 105 transmits the calibration instruction signal to the spectacle-type electronic device 1 via the communication part 91 when the calibration part 105 judges that the spectacle-type electronic device 1 has become horizontal. The calibration instruction signal may be transmitted to the spectacle-type electronic device 1 in a case in which the portable electronic device 81 judges that the detected position of the spectacle-type electronic device 1 is in a predetermined relationship with respect to the tilt that is identified, and the calibration may be performed under a condition that the spectacle-type electronic device 1 receives the calibration instruction signal.

When the processing part 77 of the spectacle-type electronic device 1 judges that the communication part 73 received the calibration instruction signal from the portable electronic device 81, the processing part 77 performs the calibration of the acceleration sensor 71.

According to the calibration method in this embodiment, the calibration part 105 judges whether the spectacle-type electronic device 1 has become horizontal, and automatically transmits the calibration instruction to the spectacle-type electronic device 1 when the condition is satisfied. Hence, a load on the wearer can be reduced, and a highly reliable calibration process can be performed.

Third Embodiment

In the first embodiment described above, in the case in which the wearer judges that the spectacle-type electronic device 1 has become horizontal, the wearer operates the operation part 85 of the portable electronic device 81 and inputs the calibration instruction. In a third embodiment, the wearer operates an operation part of the spectacle-type electronic device 1 and inputs the calibration instruction.

Figure 7:
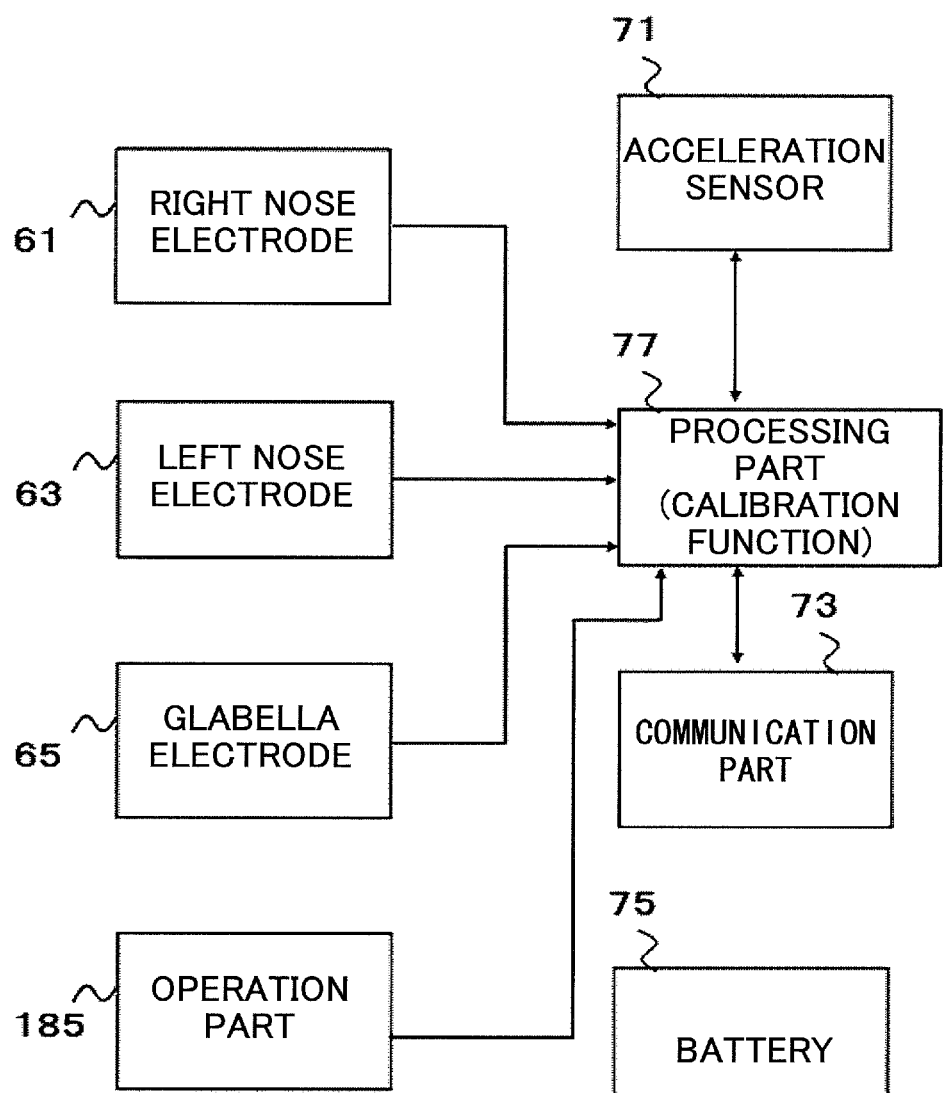
FIG. 7 is a functional block diagram of the spectacle-type electronic device in a third embodiment of the present invention.

FIG. 7 is a functional block diagram of a spectacle-type electronic device 301 in the third embodiment of the present invention.

In FIG. 7, those constituent elements that are designated by the same reference numerals as in FIG. 2 are the same as the constituent elements of the first embodiment described above.

The spectacle-type electronic device 301 has an operation part 185. When the wearer views the tilt adjusting image displayed on the display 83 of the portable electronic device 81 and judges that the image of the spectacle-type electronic device 1 matches the horizontal line indicated by the horizontal line image 115, the wearer operates the operation part 185. Hence, the processing part 77 judges that the calibration instruction is input, and performs the calibration process of the acceleration sensor 71. In other words, the calibration of the acceleration sensor 71 is performed under a condition that the calibration instruction is input to the spectacle-type electronic device 1.

In this embodiment, no communication is required between the spectacle-type electronic device 1 and the portable electronic device 81, and a configuration can thereby be simplified.

The present invention is not limited to the embodiments described above, and various variations, modifications, and substitutions may be made without departing from the scope of the present invention.

In other words, the embodiments described above perform the calibration of the acceleration sensor 71 of the spectacle-type electronic device 1 under the condition that the spectacle-type electronic device 1 has become horizontal. However, the calibration may be performed in a case in which the position of the spectacle-type electronic device becomes a predetermined position, that is other than horizontal, and is determined in advance.

In addition, in the embodiments described above, the acceleration sensor 71 is provided within the accommodation box 53 that is positioned near the temple tip 37 of the temple 11. However, the acceleration sensor 71 may be provided at a position other than the position near the temple tip 37. Further, a plurality of acceleration sensors may be provided at different positions of the spectacle-type electronic device 1.

Figure 8:
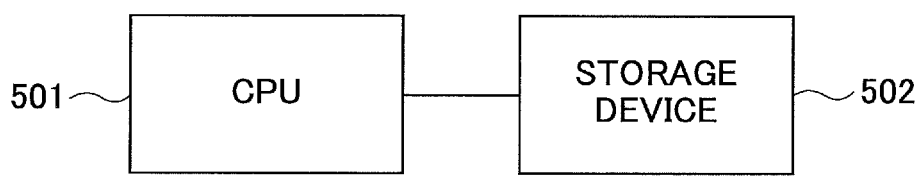
FIG. 8 is a block diagram illustrating an example of a hardware configuration of a computer.

FIG. 8 is a block diagram illustrating an example of a hardware configuration of a computer. A computer 500 illustrated in FIG. 8 includes a CPU (Central Processing Unit) 501, and a storage device 502. The CPU 501 is an example of a processor that executes one or more programs, and controls an operation of the computer 100 to function as any one of the processing parts 77 illustrated in FIG. 2 and FIG. 7, and the processing part 93 illustrated in FIG. 3. The storage device 502 stores one or more programs, and various data.

The storage device 502 may be formed by a semiconductor memory device, such as a flash memory and a USB (Universal Serial Bus) memory, and a drive, such as a magnetic disk drive, an optical disk drive, a magneto-optical disk drive, a tape drive, or the like, for example. The storage device 502 may also be formed by a non-transitory computer-readable storage medium which stores the one or more programs and the data that are used when performing the calibration process or the like.

In the embodiments described above, the present invention is applied to the spectacle-type electronic device 1 having the lenses 21 and 23. However, the present invention may also be applied to eyewear or the like having no lenses.

The present invention is applicable to a system in which the acceleration sensor of the spectacle-type electronic device is calibrated.

What is claimed is:
1. A calibration method comprising:
a first step identifying a predetermined tilt with respect to a gravity direction based on an acceleration detected by a first acceleration sensor provided in a portable device;
a second step displaying, on a display of the portable device, a tilt adjusting image for adjusting a tilt of a spectacle-type electronic device, based on an image of a wearer of the spectacle-type electronic device captured by the portable device and the predetermined tilt that is identified; and
a third step performing a calibration of a second acceleration sensor provided in the spectacle-type electronic device under a condition that a tilt of the spectacle-type electronic device is adjusted, wherein
the first step identifies a horizontal direction as the predetermined tilt with respect to the gravity direction, and
the second step displays on the display the tilt adjusting image that simultaneously includes the image that is captured, and an image of a horizontal line in the horizontal direction that is identified.

2. A calibration method comprising:
a first step identifying a predetermined tilt with respect to a gravity direction based on an acceleration detected by a first acceleration sensor provided in a portable device;
a second step displaying, on a display of the portable device, a tilt adjusting image for adjusting a tilt of a spectacle-type electronic device, based on an image of a wearer of the spectacle-type electronic device captured by the portable device and the predetermined tilt that is identified; and
a third step performing a calibration of a second acceleration sensor provided in the spectacle-type electronic device under a condition that a tilt of the spectacle-type electronic device is adjusted,
wherein the third step transmits a calibration instruction from the portable device to the spectacle-type electronic device when the portable device receives the calibration instruction while the tilt adjusting image is being displayed, and performs the calibration under a condition that the spectacle-type electronic device receives the calibration instruction.

3. The calibration method as claimed in claim 1, wherein the third step detects a position of the spectacle-type electronic device by the portable device based on feature points of the spectacle-type electronic device within the image that is captured, transmits a calibration instruction to the spectacle-type electronic device in a case in which the portable device judges that the detected position is in a predetermined relationship with respect to the tilt that is identified, and performs the calibration under a condition that the spectacle-type electronic device receives the calibration instruction.

4. The calibration method as claimed in claim 1, wherein a fourth step performs the calibration of the second acceleration sensor of the spectacle-type electronic device under a condition that a calibration instruction is input to the spectacle-type electronic device.

5. A portable device comprising:
a capturing device configured to capture an image of a wearer wearing a spectacle-type electronic device;
a first acceleration sensor; and
a processor configured to perform a process including
identifying a predetermined tilt with respect to a gravity direction based on an acceleration detected by the first acceleration sensor;
displaying, on a display, a tilt adjusting image for adjusting a tilt of the spectacle-type electronic device, based on the image that is captured and the predetermined tilt that is identified; and
transmitting, to the spectacle-type electronic device, a calibration instruction that instructs calibration of a second acceleration sensor of the spectacle-type electronic device, under a condition that a tilt of the spectacle-type electronic device is adjusted, wherein
the identifying identifies a horizontal direction as the predetermined tilt with respect to the gravity direction, and the displaying displays on the display the tilt adjusting image that simultaneously includes the image that is captured, and an image of a horizontal line in the horizontal direction that is identified.

6. A portable device comprising:
a capturing device configured to capture an image of a wearer wearing a spectacle-type electronic device;
a first acceleration sensor, and
a processor configured to perform a process including
identifying a predetermined tilt with respect to a gravity direction based on an acceleration detected by the first acceleration sensor;
displaying, on a display, a tilt adjusting image for adjusting a tilt of the spectacle-type electronic device, based on the image that is captured and the predetermined tilt that is identified; and
transmitting, to the spectacle-type electronic device, a calibration instruction that instructs calibration of a second acceleration sensor of the spectacle-type electronic device, under a condition that a tilt of the spectacle-type electronic device is adjusted,
wherein the transmitting transmits the calibration instruction to the spectacle-type electronic device when the portable device receives the calibration instruction while the tilt adjusting image is being displayed on the display, to perform the calibration under a condition that the spectacle-type electronic device receives the calibration instruction.

7. The portable device as claimed in claim 5, wherein the processor performs the process further including
detecting a position of the spectacle-type electronic device based on feature points of the spectacle-type electronic device within the image that is captured,
wherein the transmitting transmits the calibration instruction to the spectacle-type electronic device in a case in which the processor judges that the detected position is in a predetermined relationship with respect to the tilt that is identified, to perform the calibration under a condition that the spectacle-type electronic device receives the calibration instruction.

8. A non-transitory computer-readable storage medium having stored therein a program which, when executed by a computer of a portable device, causes the computer to perform a calibration process comprising:
a first procedure identifying a predetermined tilt with respect to a gravity direction based on an acceleration detected by a first acceleration sensor provided in a portable device;
a second procedure displaying, on a display of the portable device, a tilt adjusting image for adjusting a tilt of a spectacle-type electronic device, based on an image of a wearer of the spectacle-type electronic device captured by the portable device and the predetermined tilt that is identified; and
a third procedure performing a calibration of a second acceleration sensor provided in the spectacle-type electronic device under a condition that a tilt of the spectacle-type electronic device is adjusted, wherein
the first procedure identifies a horizontal direction as the predetermined tilt with respect to the gravity direction, and
the second procedure displays on the display the tilt adjusting image that simultaneously includes the image that is captured, and an image of a horizontal line in the horizontal direction that is identified.

9. A non-transitory computer-readable storage medium having stored therein a program which, when executed by a computer of a portable device, causes the computer to perform a calibration process comprising:
a first procedure identifying a predetermined tilt with respect to a gravity direction based on an acceleration detected by a first acceleration sensor provided in a portable device;
a second procedure displaying, on a display of the portable device, a tilt adjusting image for adjusting a tilt of a spectacle-type electronic device, based on an image of a wearer of the spectacle-type electronic device captured by the portable device and the predetermined tilt that is identified; and
a third procedure performing a calibration of a second acceleration sensor provided in the spectacle-type electronic device under a condition that a tilt of the spectacle-type electronic device is adjusted,
wherein the third procedure transmits a calibration instruction from the portable device to the spectacle-type electronic device when the portable device receives the calibration instruction while the tilt adjusting image is being displayed, and performs the calibration under a condition that the spectacle-type electronic device receives the calibration instruction.

10. The non-transitory computer-readable storage medium as claimed in claim 8, wherein the third procedure detects a position of the spectacle-type electronic device by the portable device based on feature points of the spectacle-type electronic device within the image that is captured, transmits a calibration instruction to the spectacle-type electronic device in a case in which the portable device judges that the detected position is in a predetermined relationship with respect to the tilt that is identified, and performs the calibration under a condition that the spectacle-type electronic device receives the calibration instruction.

11. The calibration method as claimed in claim 2, wherein the third step detects a position of the spectacle-type electronic device by the portable device based on feature points of the spectacle-type electronic device within the image that is captured, transmits a calibration instruction to the spectacle-type electronic device in a case in which the portable device judges that the detected position is in a predetermined relationship with respect to the tilt that is identified, and performs the calibration under a condition that the spectacle-type electronic device receives the calibration instruction.

12. The calibration method as claimed in claim 2, wherein a fourth step performs the calibration of the second acceleration sensor of the spectacle-type electronic device under a condition that a calibration instruction is input to the spectacle-type electronic device.

13. The portable device as claimed in claim 6, wherein the processor performs the process further including
detecting a position of the spectacle-type electronic device based on feature points of the spectacle-type electronic device within the image that is captured,
wherein the transmitting transmits the calibration instruction to the spectacle-type electronic device in a case in which the processor judges that the detected position is in a predetermined relationship with respect to the tilt that is identified, to perform the calibration under a condition that the spectacle-type electronic device receives the calibration instruction.

14. The non-transitory computer-readable storage medium as claimed in claim 9, wherein the third procedure detects a position of the spectacle-type electronic device by the portable device based on feature points of the spectacle-type electronic device within the image that is captured, transmits a calibration instruction to the spectacle-type electronic device in a case in which the portable device judges that the detected position is in a predetermined relationship with respect to the tilt that is identified, and performs the calibration under a condition that the spectacle-type electronic device receives the calibration instruction.

* * * * *